United States Patent
Gruebler et al.

(10) Patent No.: US 7,084,646 B2
(45) Date of Patent: Aug. 1, 2006

(54) METHOD OF DETECTING A GAS BUBBLE IN A LIQUID

(75) Inventors: Robert Gruebler, Graz (AT); Egon Landschuetzer, Graz (AT); Wolf-Dietrich Steinboeck, Graz (AT)

(73) Assignee: Roche Diagnostics Operations, Inc., Indianapolis, IN (US)

(*) Notice: Subject to any disclaimer, the term of this patent is extended or adjusted under 35 U.S.C. 154(b) by 0 days.

(21) Appl. No.: 10/913,753

(22) Filed: Aug. 6, 2004

(65) Prior Publication Data

US 2005/0046429 A1 Mar. 3, 2005

(30) Foreign Application Priority Data

Aug. 7, 2003 (AT) .............. A 1250/2003

(51) Int. Cl.
*G01R 27/08* (2006.01)
*G01N 27/00* (2006.01)

(52) U.S. Cl. ..................... 324/693; 324/71.1

(58) Field of Classification Search ........... 324/693, 324/71.1, 464

See application file for complete search history.

(56) References Cited

U.S. PATENT DOCUMENTS

| 4,160,713 | A | * | 7/1979 | Matsuzaki et al. | .......... 204/519 |
|---|---|---|---|---|---|
| 4,358,423 | A | * | 11/1982 | Nedetzky | ............ 422/82.02 |
| 5,144,831 | A | * | 9/1992 | Hale et al. | .......... 73/19.05 |
| 5,631,552 | A | * | 5/1997 | Ogawa et al. | ............ 324/71.1 |
| 6,831,470 | B1 | * | 12/2004 | Xie et al. | ............ 324/693 |
| 2005/0109410 | A1 | * | 5/2005 | Gilbert et al. | ............ 137/827 |

FOREIGN PATENT DOCUMENTS

| DE | 39 27 718 C1 | 3/1990 |
|---|---|---|
| EP | 0 484 876 A1 | 5/1992 |
| EP | 0 818 682 A2 | 7/1997 |
| EP | 1 054 252 A2 | 5/2000 |
| EP | 1 182 264 A2 | 2/2002 |
| JP | 2000/199763 A | 11/2000 |
| WO | WO 01/33195 A1 | 5/2001 |
| WO | WO 200133195 A1 * | 5/2001 |

* cited by examiner

*Primary Examiner*—Anjan Deb

(57) ABSTRACT

A method of detecting a gas bubble in a measuring chamber filled with a liquid. The electrical conductivity of the liquid or a variable derived therefrom is measured in the measuring chamber at a first pressure value $p_1$, and a first measured value $S_1$ is detected. The pressure in the measuring chamber is changed, the electrical conductivity of the liquid or a variable depending thereon is measured in the measuring chamber at at least a second pressure value $p_2$, and a second measured value $S_2$ is detected. The presence or lack of presence of at least one gas bubble in the liquid is detected by comparing the first measured value $S_1$ to the second measured value $S_2$.

18 Claims, 2 Drawing Sheets

METHOD OF DETECTING A GAS BUBBLE IN A LIQUID

BACKGROUND OF THE INVENTION

The present invention relates to methods of detecting a gas bubble in a liquid and, more particularly, to methods of detecting a gas bubble such as, for example, an air bubble, in a measuring chamber filled with a liquid, typically a specimen, quality-control or calibrating liquid, which chamber can comprise a measuring device or a sensor for determining a chemical or physical parameter of the liquid.

In the case of measuring chambers filled with liquids, especially biological liquids such as whole blood, serum, urine, etc., e.g., of blood gas analyzers, problems can occur in connection with the measurement of the specimen or during the calibration or quality control if the specimen, quality-control or calibrating agent fills the measuring chamber only incompletely, or if there are gas bubbles such as, for example, air bubbles situated in the liquid in the region of the sensors. Especially in the case of measuring chambers with small specimen volumes which can be configured in a mostly capillary manner, air bubbles will lead to faulty measurements, so that an effective verification must be carried out with respect to the presence or lack of presence of air bubbles.

Reference to the problem of enclosed air bubbles is made in U.S. Pat. No. 4,358,423, which bubbles distort the measuring result because the air bubbles prevent a sufficient wetting of the surface of the respectively used sensors. Measures which recognize such errors are especially necessary in automatically operating analyzers where the filling process of the measuring capillaries or the freedom from bubbles of the specimen material in the measuring capillaries must be checked in an automatic way. U.S. Pat. No. 4,358,423 provides a method to solve this problem in which the value of the resistance between at least two positions in the measuring chamber is measured, with the filling process of the measuring chamber being controlled depending on the determined variable of the measured resistance.

In the course of the measuring chamber there can be three contact points for the measurement of the electrical resistance, with a pair of the contacts each being used for the resistance measurement with the help of a changeover switch, i.e., either the first and second contacts or the second and third contacts are used. In a filling of the measuring chamber which contains air bubbles, the electrical contact between the first and second contacts is established first. It will be interrupted by the enclosed air bubble again before the section between the second and third contacts becomes electrically conductive. The electric signal derived therefrom can be used to interrupt the filling process and to signal a fault.

Air bubbles which only partly fill the cross section of the measuring channel or the measuring capillaries cannot be actually detected with the method described in U.S. Pat. No. 4,358,423. Although the resistance measurements would show slight differences in the measuring signal in such a case, they could not be differentiated from signal changes based on different conductivities of the individual specimens, which are caused by different hematocrit values, for example.

WO 01/33195 A1 discloses a method and an apparatus for the detection of bubbles in a liquid in which the liquid is in contact with a $pO^2$- or a $pCO_2$ sensor, for example. In order to verify whether a gas bubble is present in the region of the sensor, a first measured value for the gas concentration is performed at a first pressure value in the measuring chamber and thereafter the pressure is changed to a second pressure value in the measuring chamber. The gas concentration is also measured at the second pressure value and a second measured value is produced. The second measured value is compared with an expected value at the altered pressure and, depending on the difference of the two values, the presence of gas bubbles is deduced. The disadvantages in the method according to WO 01/33195 A1 are that the application is limited to the use of gas sensors. If the air bubble is situated in the region of other sensors in the measuring chamber, the same cannot be detected by this method. It is further also possible that an air bubble situated in the region of the gas sensor is pushed from the sensitive region of the electrode by the change in pressure and that as a result additional measuring components occur which distort the result of the measurement.

Finally, a device for the dynamic measurement of the bubble content of a flowing liquid is known from EP 0 484 876 B1, which comprises a device for measuring the pressure, temperature and volumetric flow rate of the liquid, with the flow rate between points of high and low pressure being measured and the bubble content of the liquid being calculated therefrom. The method substantially utilizes the change in volume of the liquid resulting from the pressure change which is dependent on the bubble content.

SUMMARY OF THE INVENTION

It is against the above background that the present invention provides certain unobvious advantages and advancements over the prior art. In particular, the inventors have recognized a need for improvements in methods of detecting a gas bubble in a liquid and, more particularly, for improvements in methods of detecting a gas bubble in a measuring chamber filled with a liquid in such a way that independent of the sensors employed in the measuring chamber a rapid and precise statement can be achieved on the presence or lack of presence of gas bubbles such as, e.g., air bubbles, in the liquid to be measured. Despite the additional check, the usual measuring process is to be maintained in a substantially unchanged way.

In accordance with one embodiment of the present invention, a method of detecting a gas bubble in a measuring chamber is provided comprising filling the measuring chamber with a liquid; measuring the electrical conductivity of the liquid or a variable derived therefrom in the measuring chamber at a first pressure value $p_1$, wherein a first measured value $S_1$ is detected; changing the pressure in the measuring chamber; measuring the electrical conductivity of the liquid or a variable depending thereon in the measuring chamber at at least a second pressure value $p_2$, wherein a second measured value $S_2$ is detected; and detecting the presence or lack of presence of at least one gas bubble in the liquid by comparing the first measured value $S_1$ to the second measured value $S_2$. The at least one gas bubble can comprise an air bubble and the liquid can comprise, for example, a specimen, a quality-control, or a calibrating liquid.

The electrical conductivity (or impedance, resistance) of a liquid or a variable derived therefrom is measured in accordance with the present invention in a measuring chamber at a first pressure value Pi and thus a first measured value $S_1$ is detected. The pressure in the measuring chamber is then changed, and the electrical conductivity of the liquid or a variable depending thereon is measured in the measuring chamber at at least a second pressure value $p_2$, and thus a second measured value $S_2$ is detected. By comparing the two measured values $S_1$ and $S_2$, the presence or lack of presence of at least one gas bubble in the liquid can be deduced. In accordance with the instant embodiment, the invention utilizes the fact that a change of the conductivity of the liquid, for example, is accompanied by changing the pressure when gas bubbles are present in the liquid. The measuring chamber can comprise at least one measuring device such as, for example, at least one sensor, which can be configured for determining a chemical or physical parameter of the liquid. The method in accordance with the present invention is not limited to the use of gas sensors and can be applied in a very simple manner in measuring chambers which are already equipped with electrodes for conductivity measurements for the purpose of checking the filling process. The method in accordance with the present invention can thus be realized without any additional built-in elements.

The present invention can further comprise forming a normalized difference value from the first and second measured values $S_1$ and $S_2$, e.g., $\Delta S/S_1$, and detecting the presence or lack of presence of at least one gas bubble in the liquid by comparing the normalized difference value with a threshold value.

It is further possible to deduce or detect the presence or lack of presence of at least one gas bubble in the liquid by comparing the ratio of the measured values $S_1/S_2$ with a threshold value.

In accordance with another embodiment of the present invention, the method can further comprise, typically after changing the pressure in the measuring chamber, determining the time progress of the second measured value $S_2$ of the electrical conductivity of the liquid or a variable depending thereon, and detecting the presence or lack of presence of at least one gas bubble in the liquid by comparing a time-extrapolated value with a threshold value. If desired, the detected measured values can be extrapolated to time regions outside of the measuring window (e.g., with the help of predetermined curve models).

For example, a threshold value for the normalized difference value $\Delta S/S_1$ can be predetermined and the presence of a gas bubble can be indicated when the value falls below this threshold value. Depending on the type and basic setting of the analyzer it is possible to reject the specimen and to automatically start a new specimen-taking cycle.

Although it would also be possible to increase the pressure in the measuring chamber by between about 100 and about 300 mbar for the second measured value, the bubble detection can be integrated especially well in the usual measuring sequence of an analyzer when the change of the pressure in the specimen chamber is carried out in accordance with the invention in the form of a pressure decrease in the region of between about 100 and about 400 mbar, typically by about 250 mbar. The start of the washing process in the measuring chamber can be used specifically for the bubble detection, for example.

A change in the electrical conductivity of the liquid, e.g., a specimen, such as a blood sample, can occur during a change in the pressure as a result of the movement of the liquid column. Although the present invention is not limited to specific advantages or functionality, it therefore can be advantageous when after the change in the pressure and prior to the detection of the second measured value $S_2$ a waiting period is observed. Thus, the present invention can further comprise, in accordance with yet another embodiment, observing a waiting time following changing the pressure in the measuring chamber and prior to the detection of the second measured value $S_2$.

In order to exclude changes of the gas partial pressure of the liquid in the case of a rapid change of pressure, it can also be advantageous when the gas bubble detection in the liquid is performed after the actual determination of a chemical or physical parameter of the liquid.

In accordance with still another embodiment of the present invention, the method can further comprise employing electrical points of contact at an entrance and/or exit of the measuring chamber for measuring the electrical conductivity of the liquid or a value derived therefrom. In accordance with yet still another embodiment of the present invention, it is also possible to measure the electrical conductivity of the liquid or a value derived therefrom with respect to at least one further contact point positioned between the entrance or input and the exit or output of the measuring chamber, and optionally performing a localization of the at least one gas bubble by comparing with the conductivity values of at least two sections of the measuring chamber.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiment(s) of the present invention.

DETAILED DESCRIPTION OF THE INVENTION

Figure 1:
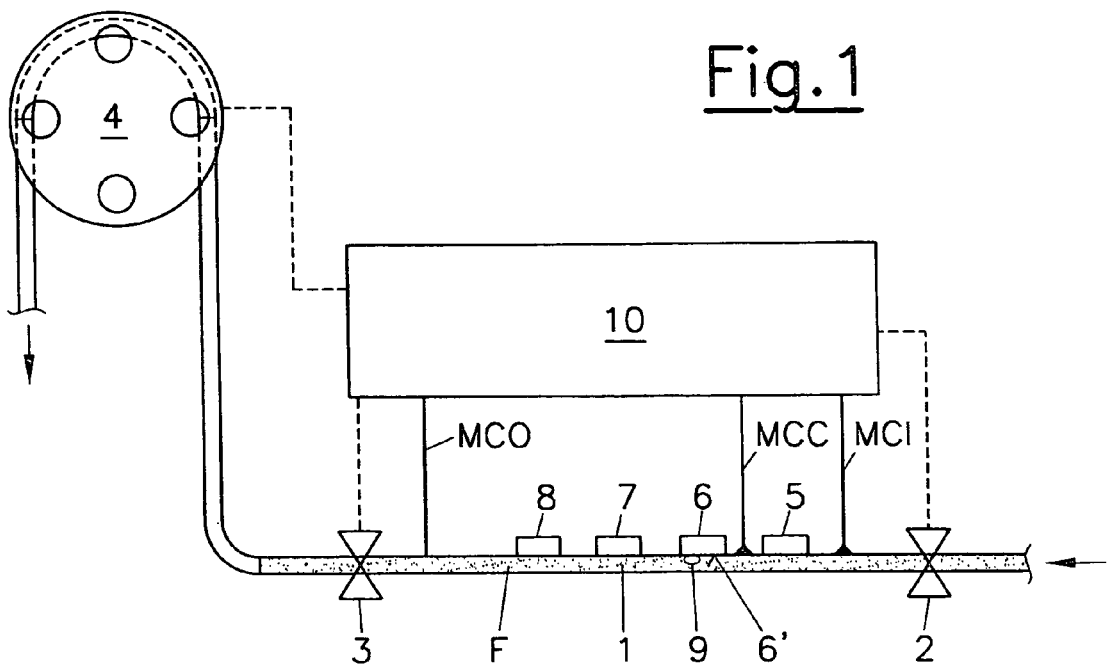
FIG. 1 is a schematic illustration showing an apparatus for performing a method of detecting a gas bubble in a measuring chamber filled with a liquid in accordance with the principals of the present invention.

Referring initially to FIG. 1, a schematic representation of a measuring chamber 1 is provided in accordance with one embodiment of the present invention, which chamber 1 is filled with a liquid F, e.g., a specimen, quality-control, or calibrating liquid, and can be configured as a flow-rate measuring chamber. Measuring chamber 1 can comprise on the input side an inlet valve 2 and an outlet valve 3 on the outlet side, and the liquid or specimen transport can be effected with the help of a hose pump 4. The measuring chamber I can further comprise several sensors 5 through 8 which are in contact with the liquid F in the measuring chamber 1. The measuring chamber can also comprise an optical apparatus for measuring a physical or chemical variable, e.g., the hemoglobin concentration, as is explained for example in EP 0 818 682 A2 or in EP 1 054 252 A2.

An air bubble 9 is shown in the region of the sensitive surface 6' of the sensor 6, which bubble 9, when not recognized, can adulterate the measured value of the sensor 6. Electrical contact points MCI and MCO can be situated on the input side as well as the output side of the measuring chamber 1, which contact points can be connected with an analyzing and control unit 10. Further contact points between measuring chamber input and measuring chamber output or between the contacts MCI and MCO are possible; for example, a contact point MCC can be arranged between the sensors 5 and 6. In order to measure the electrical conductivity, the electrical resistance or a variable derived therefrom, a measuring section can be provided over the entire measuring chamber 1 or over a part of the measuring chamber 1, depending on the contact points between which the conductivity is measured. The described configuration of the contact points is also suitable for measuring the filling level of the measuring chamber 1.

In accordance with an embodiment of the present invention, a so-called expansion check can be performed for the detection of at least one gas bubble after the actual measuring of the sample liquid F with the help of at least one of the sensors 5 through 8. Specifically, a first conductivity measured value $S_1$ at pressure $p_1$ is detected (e.g., at atmospheric pressure) with closed valves 2 and 3 and a suction pressure is built up in front of the measuring chamber 1 with the help of hose pump 4, which suction pressure, depending on the runtime of the pump 4 and the volume of the line system, is situated in the region of between about 100 and about 400 mbar, typically at approximately 250 mbar. Thereafter, the suction-side valve 3 is opened so that the negative pressure comes to bear. Then, after a short waiting period of 0.2 s, for example, in order to allow movements of the liquid column to abate as a result of the change in pressure, a conductivity measurement $S_2''$ is performed in the measuring chamber. Then after 0.5 s, a conductivity measurement $S_2'$ is performed, and finally after a further 0.5 s (a total of approx. 1.2 s after the opening of the valve 2) a conductivity measurement $S_2$ is performed. The last of the measurements $S_2$ is placed at a ratio to the basic measurement $S_1$ and the quotient is evaluated.

Figure 2:
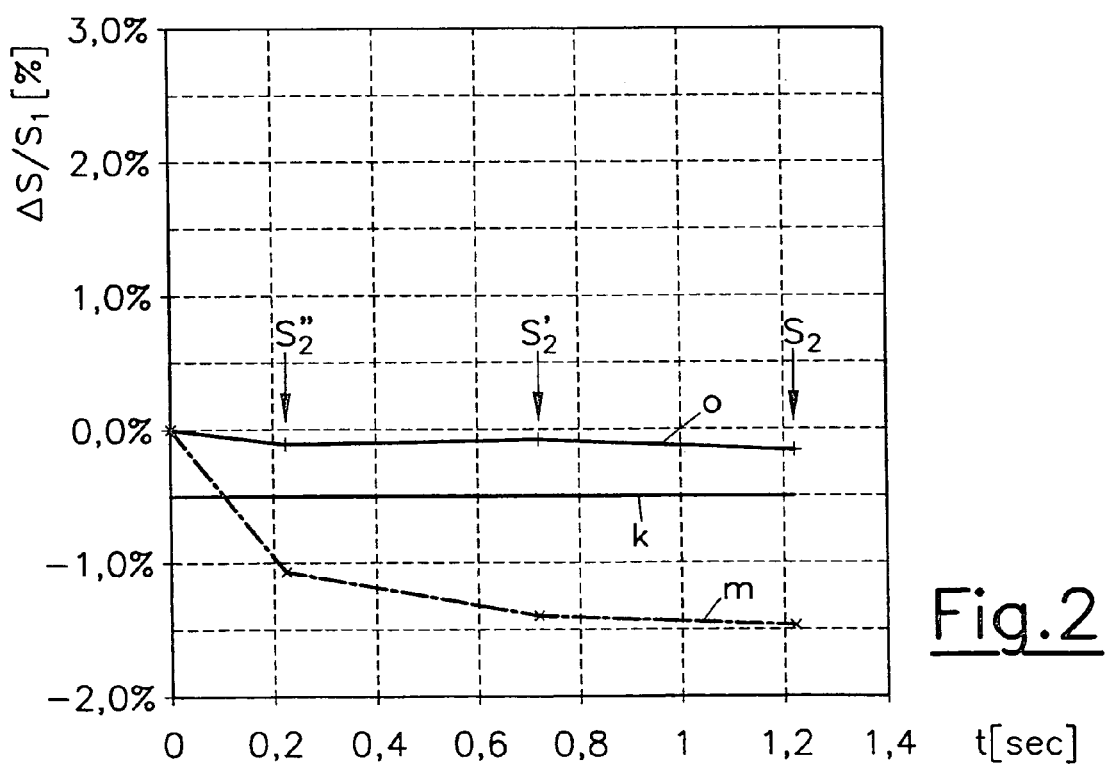
FIGS. 2–4 show measuring diagrams of different specimen and quality-control liquids with and without an enclosed gas bubble in accordance with the principals of the present invention.
Figure 3:
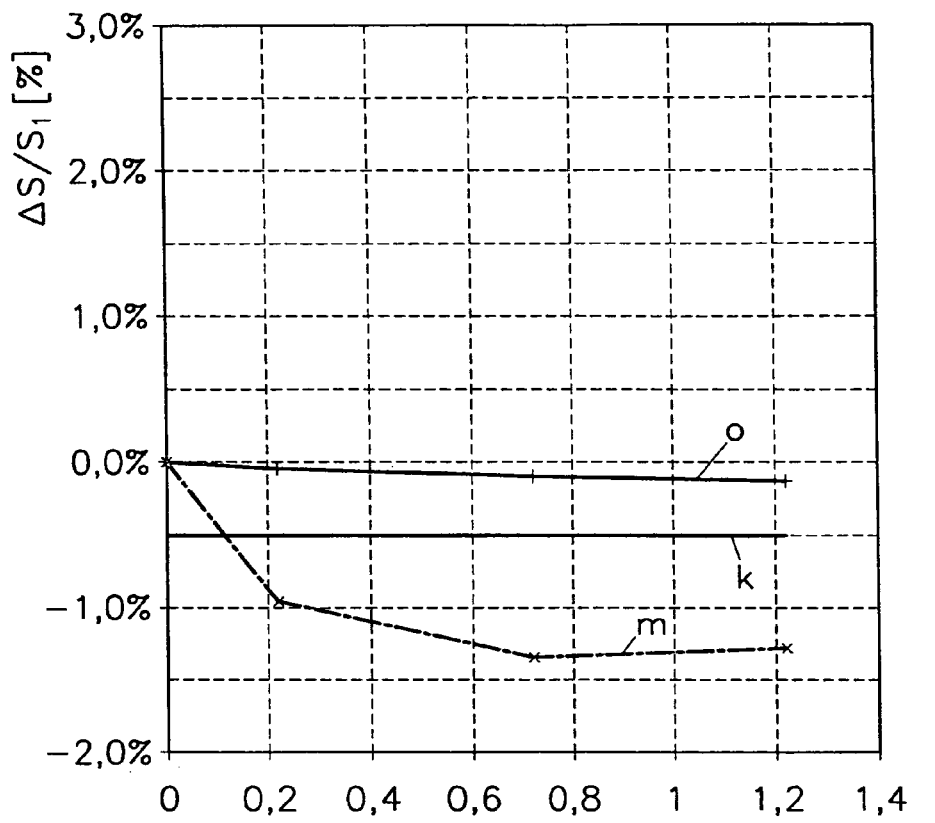
Figure 4:
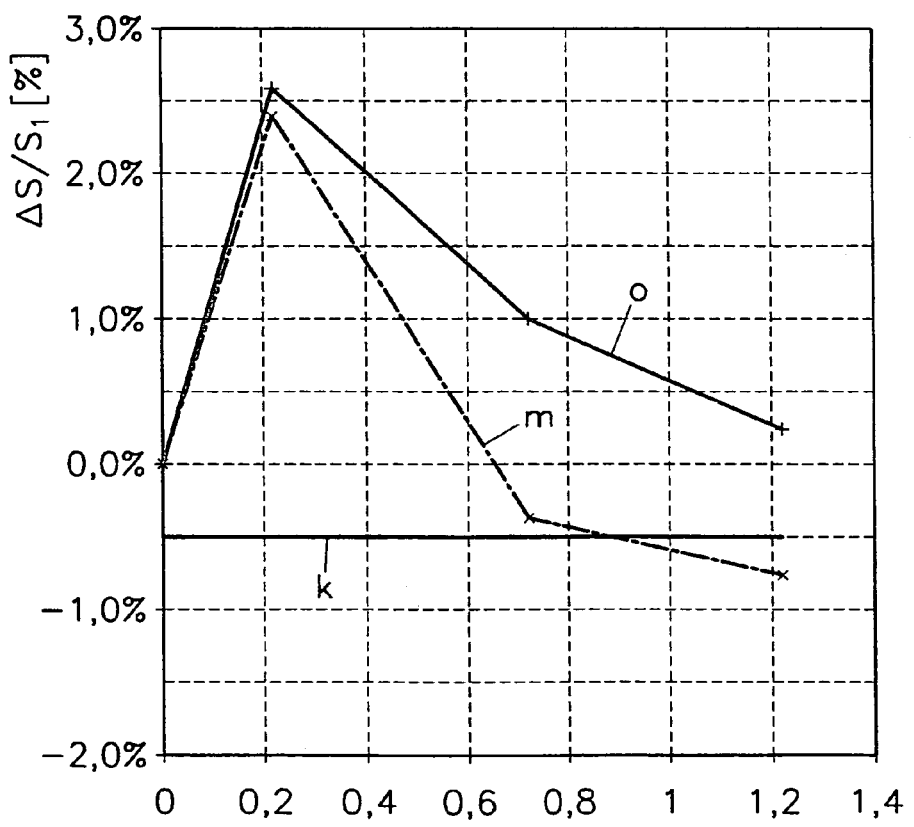

It is also possible, as is shown in the diagrams of FIGS. 2 through 4, to state the conductivity at altered pressure $p_2$ as a $\Delta\%$-value relating to the conductivity $S_1$ at output pressure $p_1$ in the form $\Delta S/S_1$.

In the diagrams according to FIGS. 2 through 4, the normalized difference value of the two measured values $\Delta S/S_1$ is entered in percent depending on the time t. Moreover, a threshold value k is entered which states the presence of an air or gas bubble if a value drops below the threshold value.

FIG. 2 shows the conditions in measuring a quality-control liquid with an air bubble (curve m) and without an air bubble (curve o). The curve m clearly shows a conductivity drop in the percentage range which can be regarded as significant for the presence of an air bubble.

FIG. 3 shows a control measurement based on the example of a plasma specimen, with m showing the measuring curve and o the measuring curve without the gas bubble.

Finally, FIG. 4 shows the measuring situation for a blood sample. A rise in the electrical conductivity can be recognized both for the blood sample with (m) as well as for the blood sample without (o) a gas bubble, which rise in the conductivity is caused in the applied measuring configuration by a movement of the liquid caused by the pressure reduction and the thus resulting change in the spatial orientation of the blood cells. Similar effects can also be expected in other aqueous emulsions and suspensions. After some time however the measured values of the blood specimen without the gas bubble move towards the initial value again, whereas the measured values of the blood specimen with the gas bubble drop below the threshold value. The time progress of the measuring curves can also be extrapolated beyond the actual measuring range.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A method of detecting a gas bubble in a measuring chamber comprising:
   filling said measuring chamber with a liquid;
   measuring the electrical conductivity of said liquid or a variable derived therefrom in said measuring chamber at a first pressure value $p_1$, wherein a first measured value $S_1$ is detected;
   changing the pressure in said measuring chamber;
   measuring the electrical conductivity of said liquid or a variable depending thereon in said measuring chamber at at least a second pressure value $p_2$, wherein a second measured value $S_2$ is detected; and
   detecting the presence or lack of presence of at least one gas bubble in said liquid by comparing said first measured value $S_1$ to said second measured value $S_2$.

2. The method of claim 1, wherein said at least one gas bubble comprises an air bubble.

3. The method of claim 1, wherein said liquid is a specimen, a quality-control, or a calibrating liquid.

4. The method of claim 1, wherein said measuring chamber comprises at least one measuring device.

5. The method of claim 4, wherein said measuring device comprises at least one sensor.

6. The method of claim 4, wherein said measuring device is configured for determining a chemical or physical parameter of said liquid.

7. The method of claim 1 further comprising
   forming a normalized difference value from said first measured value $S_1$ and said second measured value $S_2$, and detecting the presence or lack of presence of said at least one gas bubble in said liquid by comparing said normalized difference value with a threshold value.

8. The method of claim 7, wherein said normalized difference value is $\Delta S/S_1$.

9. The method of claim 1 further comprising detecting the presence or lack of presence of said at least one gas bubble in said liquid by comparing the ratio of said measured values $S_2/S_1$ with a threshold value.

10. The method of claim 1 further comprising
determining the time progress of said second measured value $S_2$ of said electrical conductivity of said liquid or a variable depending thereon following said changing the pressure in said measuring chamber; and
detecting the presence or lack of presence of said at least one gas bubble in said liquid by comparing a time-extrapolated value with a threshold value.

11. The method of claim 1, wherein said changing the pressure in said measuring chamber comprises increasing the pressure in said measuring chamber by about 100 to about 300 mbar.

12. The method of claim 1, wherein said changing the pressure in said measuring chamber comprises decreasing the pressure in said measuring chamber by about 100 to about 400 mbar.

13. The method of claim 1, wherein said changing the pressure in said measuring chamber comprises decreasing the pressure in said measuring chamber by about 250 mbar.

14. The method of claim 1 further comprising observing a waiting time following said changing the pressure in said measuring chamber and prior to the detection of said second measured value $S_2$.

15. The method of claim 1, wherein said detecting the presence or lack of presence of said at least one gas bubble in said liquid is performed after an actual determination of a chemical or physical parameter of said liquid.

16. The method of claim 1 further comprising employing electrical points of contact at an entrance and exit of said measuring chamber for measuring the electrical conductivity of said liquid or a variable derived therefrom.

17. The method of claim 16, wherein the electrical conductivity of said liquid or a variable derived therefrom is measured with respect to at least one further contact point positioned between said entrance and said exit of said measuring chamber.

18. The method of claim 17 further comprising performing a localization of said at least one gas bubble by comparing the conductivity values of at least two sections of said measuring chamber.

* * * * *